US006559951B2

US 6,559,951 B2

(12) United States Patent
Ishikawa et al.

(10) Patent No.: US 6,559,951 B2
(45) Date of Patent: May 6, 2003

(54) AIR REFRACTOMETER

(75) Inventors: Jun Ishikawa, Tsukuba (JP);
Morimasa Ueda, Tsukuba (JP); Hiroki Masuda, Tsukuba (JP); Yutaka Kuriyama, Tsukuba (JP)

(73) Assignees: Kazumasa Kusaka, Director General of National Institute of Advanced Industrial Science and Technology, Ministry of Economy, Trade and Industry, Tokyo (JP); Mitutoyo Corporation, Kawasaki (JP)

( * ) Notice: Subject to any disclaimer, the term of this patent is extended or adjusted under 35 U.S.C. 154(b) by 75 days.

(21) Appl. No.: 09/817,188

(22) Filed: Mar. 27, 2001

(65) Prior Publication Data

US 2001/0043334 A1 Nov. 22, 2001

(30) Foreign Application Priority Data

Mar. 8, 2000 (JP) ........................ 2000-089224

(51) Int. Cl.$^7$ ................................. G01B 9/02
(52) U.S. Cl. ...................................... 356/517
(58) Field of Search ................. 356/517, 492, 356/493, 491, 361, 349, 351

(56) References Cited

U.S. PATENT DOCUMENTS 5,764,362 A * 6/1998 Hill et al. .................. 356/358
6,124,931 A * 9/2000 Hill .......................... 356/361
6,407,816 B1 * 6/2002 De Groot et al. .......... 356/517

OTHER PUBLICATIONS

Chang et al., "Development of an Air Refractometer and Evaluation of its Performance", *International Conference of EUSPEN*, pp. 145–148.
"Development of Air Refractometer", Proceedings of JSPE Spring Meeting, 1994, pp. 451–452.

* cited by examiner

*Primary Examiner*—Robert H. Kim
*Assistant Examiner*—Irakli Kiknadze
(74) *Attorney, Agent, or Firm*—Oliff & Berridge, PLC

(57) ABSTRACT

An optical measuring light path formed by a vacuum-side laser beam (Pa) as a reference standard and an optical measuring light path formed by a gas-side laser beam (Pb) as a dimension to be measured are coaxially located sandwiching a movable end (optical transparent body 12) of a vacuum container (11) in order to satisfy Abbe's principle requiring linear disposition of the reference standard and the dimension to be measured in measurement direction, thereby reducing measurement error in measuring air refractive index and improving measurement accuracy therefor.

8 Claims, 1 Drawing Sheet

AIR REFRACTOMETER

BACKGROUND OF THE INVENTION

1. Field of the Invention

The present invention relates to an air refractometer for measuring a refractive index of various gases.

2. Description of Related Art

Conventionally, a refractometer has been used for measuring refractive index of air. The refractometer has a container with an optical path of a laser beam from a laser interferometer formed therein, where the refractive index of the air is obtained from a difference between a measured value of the laser interferometer when the inside of the container is vacuum and a measured value of the laser interferometer when the air is introduced in the container ("Development of Air Refractometer", Proceedings of JSPE Spring Meeting, 1994, P. 451, 452).

However, since such refractometer alternately creates vacuum and atmospheric condition within a single container, the container etc. can be deformed according to pressure change between the vacuum and atmosphere, so that the accuracy for measuring the refractive index cannot be improved on account of the deformation.

In order to overcome the above disadvantage, another refractometer has been proposed, the refractometer having two laser interferometers, i.e. a laser interferometer using a laser beam advancing in the vacuum and a laser interferometer using a laser beam advancing in the air, thus measuring refractive index of the air from the measured values of the laser interferometers ("Development of an Air Refractometer and Evaluation of its Performance", 1999, 1st International Conference of EUSPEN, P. 145–148).

Specifically, the refractometer uses two laser beams split from a single laser beam. A vacuum container made of metallic bellows is provided to a part of the optical path of the laser beam, the vacuum container having a window on a movable end thereof. One of the laser beams advances through the inside of the vacuum container to be reflected by the window to be incident on one of the laser interferometers. The other laser beam advances through the inside of the vacuum container to be transmitted through the window and further advances through the air to be reflected by a reflector disposed thereahead to be incident on the other laser interferometer. The laser beams are mutually parallel and are of the same advance direction.

Thus arranged refractometer obtains the refractive index of test gas from measured value obtained by measuring a movement of the vacuum optical path caused by moving the movable end of the vacuum container with one of the laser interferometers and by measuring a movement of the air optical path with the other laser interferometer.

However, since the vacuum optical path as a reference standard and the air optical path as a dimension to be measured are disposed in parallel, the refractometer using two laser interferometers does not satisfy Abbe's principle requiring linear disposition of the reference standard and the workpiece in measurement direction, thus being likely to cause measurement error according to the Abbe's principle.

SUMMARY OF THE INVENTION

The present invention adopts following arrangement to provide an air refractometer capable of reducing the measurement error by satisfying Abbe's principle, thus improving measurement accuracy.

According to an aspect of the present invention, an air refractometer has: a vacuum container, the length of the vacuum container being variable in longitudinal direction; a vacuum-side laser beam advancing inside the vacuum container in the longitudinal direction; a vacuum-side laser interferometer using the vacuum-side laser beam; a gas-side laser beam parallel to the vacuum-side laser beam and advancing inside a space of a test gas; a gas-side laser interferometer using the gas-side laser beam; a drive mechanism for driving a movable end of the vacuum container along the longitudinal direction; a vacuum-side reflector provided to a vacuum-side of the movable end of the vacuum container for reflecting the vacuum-side laser beam; and a gas-side reflector provided on a test gas side of the movable end for reflecting the gas-side laser beam, a movement of the vacuum-side reflector being measured by the vacuum-side laser interferometer, a movement of the gas-side reflector being measured by the gas-side laser interferometer, the refractive index of the test gas being measured based on the measured values, where the vacuum-side laser beam and the gas-side laser beam are split from a single laser beam and are respectively introduced to the vacuum-side laser interferometer and the gas-side laser interferometer through a single-mode light-waveguides, the respective laser beams irradiated from the respective single-mode light-waveguides being optical measuring light paths between the respective laser interferometers and the respective reflectors, and where the optical measuring light path formed by the vacuum-side laser beam and the optical measuring light path formed by the gas-side laser beam are coaxially located sandwiching the movable end of the vacuum container.

According to the above arrangement, in the two laser beams split from the single laser beam, the vacuum-side laser beam is introduced to the vacuum-side laser interferometer through the single-mode light-waveguide to advance in the inside of the vacuum container, which is reflected by the vacuum-side reflector to be incident on the vacuum-side laser interferometer. On the other hand, the gas-side laser beam is introduced to the gas-side laser interferometer through the single-mode light-waveguide to advance in the space of the test gas, which is reflected by the gas-side reflector to be incident on the gas-side laser interferometer. The movement of the optical measuring light path caused by moving the movable end of the vacuum container between the vacuum-side laser interferometer and the vacuum-side reflector is measured by the vacuum-side laser interferometer. The movement of the optical measuring light path between the gas-side laser interferometer and the gas-side reflector is measured by the gas-side laser interferometer, thus obtaining the refractive index of the test gas based on the measured values.

Here, since the optical measuring light path formed by the vacuum-side laser beam as the reference standard and the optical measuring light path formed by the gas-side laser beam as the dimension to be measured are coaxially positioned sandwiching the movable end of the vacuum container, the Abbe's principle requiring linear disposition of the reference standard and the workpiece can be satisfied. Accordingly, the measurement error in measuring the air refractive index can be reduced, thus improving measurement accuracy.

In the present invention, the vacuum-side reflector and the gas-side reflector may preferably be provided on either a vacuum side or a gas side of an optical transparent body provided on the movable end, the vacuum-side reflector and the gas-side reflector being formed by a reflective film having a reflective surface of high reflectivity on both sides thereof.

Accordingly, since the reflective film is formed on one side of the optical transparent body, the reflectors can be easily formed on both sides of the movable end, i.e. the vacuum-side and the gas-side, of the vacuum container.

In the present invention, an attitude of the single-mode light-waveguide may preferably be fixed so that an optical coupling efficiency of the vacuum-side laser beam and the gas-side laser beam respectively irradiated from the single-mode light-waveguides is more than or the same as a predetermined value.

Accordingly, since the attitude of the single-mode light-waveguides is fixed so that the optical coupling efficiency of the vacuum-side laser beam and the gas-side laser beam respectively irradiated from the single-mode light-waveguides is more than or the same as a predetermined value, the respective laser beams can be optically located substantially coaxial. In other words, the optical measuring path formed by the vacuum-side laser beam and the optical measuring path formed by the gas-side laser beam can be accurately located on the same axis.

In the above arrangement, an attitude of the reflector may preferably be fixed so that an optical coupling efficiency of the laser beam irradiated from either one of the single-mode light-waveguides and the one of the laser beam reflected by the reflector is more than or the same as a predetermined value.

In the above, while the optical measuring light path formed by the vacuum-side laser beam and the optical measuring light path formed by the gas-side laser beam are located coaxially, the attitude of the reflectors is fixed so that the coupling efficiency between, for instance, the vacuum-side laser beam irradiated from the single-mode light-waveguide and the vacuum-side laser beam reflected by the vacuum-side reflector is more than or the same as a predetermined value. Accordingly, the reflectors can be securely positioned substantially orthogonal with the respective laser beams, thus further improving the measurement accuracy.

In the above, the vacuum-side laser interferometer may preferably measure a frequency of interference fringes by the vacuum-side laser beam and the gas-side laser interferometer may preferably measure a frequency of the interference fringes by the gas-side laser beam, and, while moving the respective reflectors disposed on the movable end at a substantially uniform speed, respective measured values measured by the respective laser interferometers may preferably be multiplied by a frequency multiplying means having the same predetermined multiplying ratio, one of the multiplied measured values being counted as a reference clock of a frequency counter, the other multiplied measured values being counted as a counter clock of the frequency counter, thus obtaining a refractive index of a test gas from the measured values.

Accordingly, since the refractive index of the test gas is measured not by the number of the interference fringes measured by the respective laser interferometers but by the frequency of the interference fringes measured by the respective laser interferometers, the measurement can be conducted with high resolution.

In the present invention, the measured value measured by the vacuum-side laser interferometer may preferably be fed back to a drive controller for controlling the drive mechanism and the uniform movement of the reflector is controlled based on comparison between the feedback information and a predetermined command value of a movement speed, and the drive mechanism may preferably include: a drive body for the movable end fixed thereon; a single drive roller to be rotated in a drive direction of the drive body to drive the drive body while being in contact with the drive body; and a guide mechanism for holding the drive body in a predetermined attitude through a fluid.

Since the uniform movement of the reflectors (movable end of the vacuum container) is controlled by comparing feedback information of the value measured by the vacuum-side laser interferometer fed back to the drive controller and the predetermined command value of the moving speed, the uniform movement of the reflectors can be controlled with high accuracy.

Further, since the drive body is maintained in a predetermined attitude by the guide mechanism holding through a fluid, the drive body can be held in the predetermined attitude without mechanical distortion. Furthermore, since the drive body is driven by rotating the single drive roller while being in contact with the drive body, mechanical constraint of the drive body can be limited to a single portion of the contact portion against the drive roller.

In the above arrangement, the fluid of the guide mechanism may preferably be the test gas.

Since the test gas is used as the fluid of the guide mechanism, the measurement accuracy is not decreased even when the fluid of the guide mechanism and the test gas inside the space for the gas-side laser beam to advance are mixed.

Alternatively, the fluid of the guide mechanism may preferably be air and the guide mechanism includes an exhaust-collecting air bearing.

Accordingly, since the air is used as the fluid of the guide mechanism and the guide mechanism includes the exhaust-collecting air bearing, the fluid of the guide mechanism and the test gas for the gas-side laser beam to advance are not mixed, thus not deteriorating the measurement accuracy.

DETAILED DESCRIPTION OF PREFERRED EMBODIMENT(S)

Figure 1:
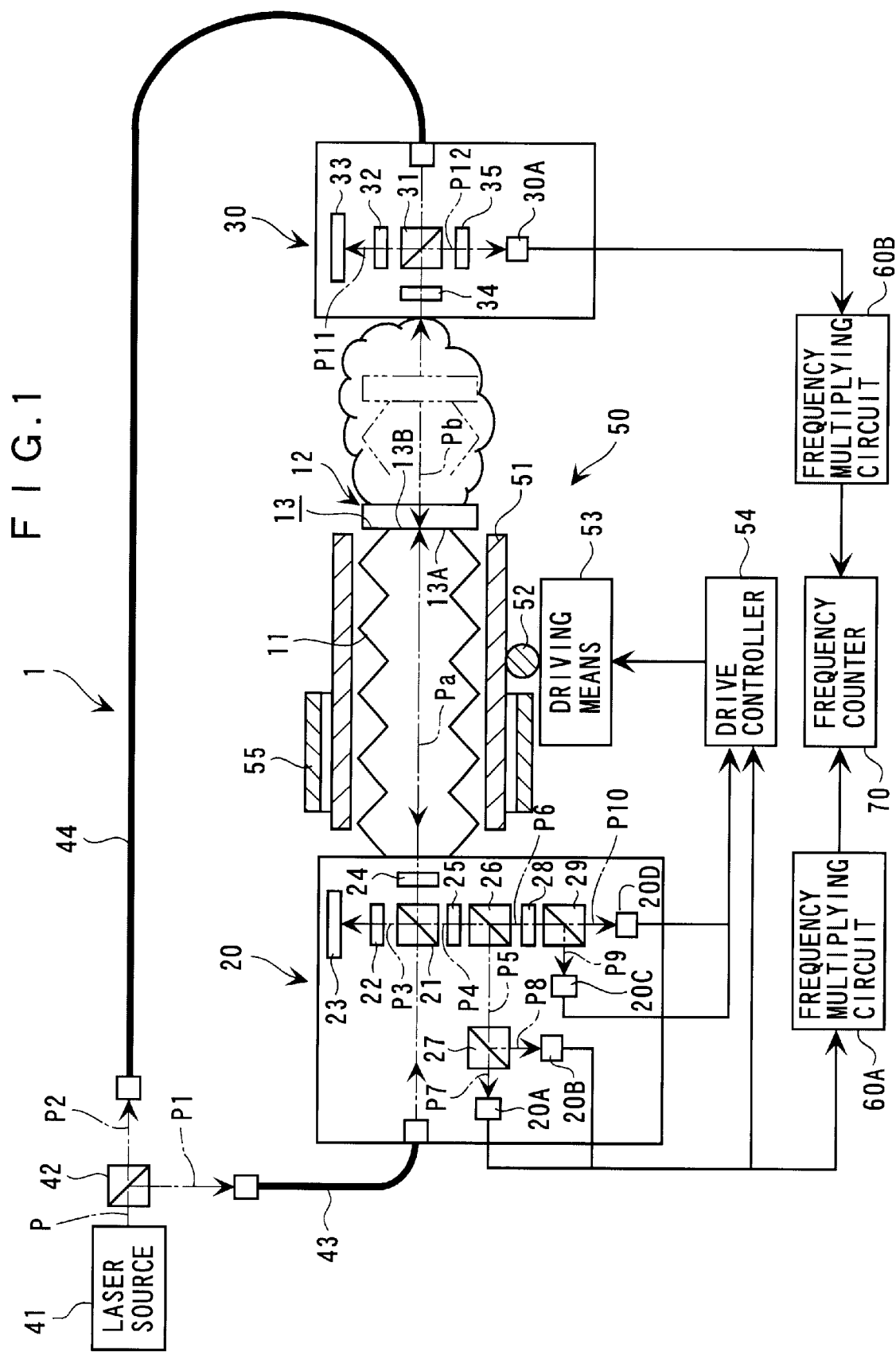
FIG. 1 is a general block diagram showing an air refractometer according to an embodiment of the present invention.

An embodiment of the present invention will be described below with reference to attached drawing.

FIG. 1 shows a general block diagram of an air refractometer according to an embodiment of the present invention.

The refractometer 1 has a vacuum-side laser beam Pa advancing in a vacuum container 11 having variable longitudinal dimension, a vacuum-side laser interferometer 20 using the vacuum-side laser beam Pa, a gas-side laser beam Pb parallel to the vacuum-side laser beam Pa and advancing in a space of the test gas, and a gas-side laser interferometer 30 using the gas-side laser beam Pb. The vacuum-side laser beam Pa and the gas-side laser beam Pb are split from a single laser beam P irradiated from a laser source 41.

The vacuum container 11 is constructed by a metallic bellows with an inside thereof being vacuum and an outside thereof surrounded by the test gas space.

An end of the vacuum container 11 is fixed to the vacuum-side laser interferometer 20. The other end (referred to as a movable end hereinafter) of the vacuum container 11 is movable along a longitudinal direction of the vacuum container 11. An optical transparent body 12 is disposed on the movable end of the vacuum container 11, the optical transparent body 12 having a reflective film 13 on one side thereof. The reflective layer 13 has reflective surfaces with high reflectivity on both sides thereof. Specifically, the reflective surface of the reflective film 13 on the vacuum side is a vacuum-side reflector 13A and the reflective surface on the test gas side is a gas-side reflector 13B, the reflectors 13A and 13B being substantially orthogonal with the vacuum-side laser beam Pa and the gas-side laser beam Pb respectively.

The vacuum-side laser beam Pa and the gas-side laser beam Pb are coaxially positioned sandwiching the movable end of the vacuum container 11, i.e. the optical transparent body 12. The vacuum-side laser interferometer 20 and the gas interferometer 30 also sandwich the optical transparent body 12, so that the vacuum-side laser beam Pa and the gas-side laser beam Pb form optical measuring light paths between the respective laser interferometers 20, 30 and the reflectors 13A, 13B.

The optical transparent body 12 is movable along the laser beam by a drive mechanism 50. The vacuum container 11 stretches and contracts in accordance with the movement of the optical transparent body 12.

The drive mechanism 50 has a drive body 51 having the optical transparent body being fixed thereon, a single drive roller 52 rotating in a driving direction of the drive body 51 while being in contact therewith for moving the drive body 51 at a constant speed, a drive means 53 for driving the drive roller, and a guide mechanism 55 for holding the drive body 51 through a fluid at a predetermined attitude. The drive mechanism 51 is controlled at a constant speed by a below-described drive controller 54.

The single laser beam P irradiated by the laser source 41 is split into the two laser beams P1 and P2 by a beam splitter 42. The laser beams P1 and P2 are respectively introduced to the vacuum-side laser interferometer 20 and the gas-side laser interferometer 30 through polarization maintaining fibers 43 and 44 as a single-mode light-waveguide.

After the laser beam PI is introduced to the inside of the vacuum-side laser interferometer 20 through the polarization maintaining fiber 43, the laser beam P1 is split into two laser beams P3 and Pa by a polarizing beam splitter 21. The laser beam P3 reflected by the polarizing beam splitter 21 is transmitted through a quarter-wave plate 22 to be reflected by a fixed mirror 23 and returns to the polarizing beam splitter 21 after being transmitted through a quarter-wave plate 22. On the other hand, the vacuum-side laser beam Pa transmitted through the polarizing beam splitter 21 advances through the inside of the vacuum container after being transmitted through the quarter-wave plate 24 to be reflected by the vacuum-side reflector 13A and returns to the polarizing beam splitter 21 after being transmitted through the quarter-wave plate 24. Since the optical-path difference is generated between the laser beam P3 and the vacuum-side laser beam Pa, interference fringes (not shown) are formed on the polarizing beam splitter 21.

The laser beam P4 joined at the polarizing beam splitter 21 is transmitted through a half-wave plate 25 to be split into two laser beams P5 and P6.

The laser beam P5 reflected by the beam splitter 26 is further split into two laser beams P7 and P8 by a polarizing beam splitter 27. The frequency of the interference fringes of the two laser beams P7 and P8 are detected respectively by sensors 20A and 20B.

On the other hand, the laser beam P6 transmitted through a beam splitter 26 is split further into two laser beams P9 and P10 by a polarizing beam splitter 29. The frequency of the interference fringes of the two laser beams P9 and P10 are detected respectively by sensors 20C and 20D.

On the other hand, after the laser beam P2 is introduced to the inside of the gas-side laser interferometer 30 through the polarization maintaining fiber 44, the laser beam P2 is split into two laser beams P11 and Pb by a polarizing beam splitter 31. The laser beam P11 reflected by the polarizing beam splitter 31 is transmitted through the quarter-wave plate 32 to be reflected by a fixed reflector 33 and returns to the polarizing beam splitter 31 after being transmitted through the quarter-wave plate 32. On the other hand, the laser beam Pb transmitted through the polarizing beam splitter 31 is transmitted through a quarter-wave plate 34 to advance in the space of the test gas to be reflected by the gas-side reflector 13B and returns to the polarizing beam splitter 31 being transmitted through the quarter-wave plate 34. Since the optical-path difference is generated between the laser beam P11 and the gas-side laser beam Pb, interference fringes (not shown) are formed on the polarizing beam splitter 31.

A laser beam P12 joined at the polarizing beam splitter 31 transmits through a polarizing plate 35 and a frequency of the interference fringes of the laser beam P12 is detected by a sensor 30A.

The frequency of the interference fringes detected by the sensors 20A and 20B of the vacuum-side laser interferometer 20 is thousand times multiplied by a frequency multiplying circuit 60A as a multiplying means to 10 MHz, which is counted as a reference clock of a frequency counter 70. On the other hand, the frequency of the interference fringes detected by the sensor 30A of the gas-side laser interferometer 30 is thousand times multiplied by the frequency multiplying circuit 60B as another multiplying means, which is counted as a counter clock of a frequency counter 70.

The ratio between the frequency of the interference fringes of the vacuum-side laser interferometer 20 and the frequency of the interference fringes of the vacuum-side laser interferometer 30 is represented as a ratio of a measured frequency value fc against the reference clock 10 MHz, so that a refractive index n of the test gas relative to vacuum can be represented as: n=fc/10 MHz.

The measured value sensed by the vacuum-side laser interferometer is fed back to the drive controller 54, whereby the uniform movement of the optical transparent body 12 (i.e. drive body 51) at a constant speed is controlled by comparing the feedback information and a predetermined command value of the movement speed.

In order to detect a position and moving direction of the movable end (optical transparent body 12) of the vacuum container 11, a frequency of the interference fringes detected by the sensors 20A to 20D of the vacuum-side laser interferometer 20 is used. Specifically, two-phase sine curves with 90 degrees phase are used, and in order to obtain the two-phase sine curves as a stable signal, four-phase sine curves respectively having 90 degrees phase difference are detected. Stable two-phase sine curves are obtained based on differential of the four-phased sine curves, whose information is compared with the predetermined command value of the moving speed to control the movement of the movable end (respective reflectors 13A and 13B) at a constant speed.

Next, a function of the present embodiment will be described below.

Initially, in measuring the refractive index of the test gas, the attitude of the polarization maintaining fibers 43 and 44 and the optical transparent body 12 (respective reflectors 13A and 13B) is fixed.

The attitude of the polarization maintaining fiber 43 and 44 is fixed so that optical coupling efficiencies of the laser beams P1 and P2 (Pa and Pb) irradiated from the respective polarization maintaining fibers 43 and 44 are more than or the same as a predetermined value. Specifically, the attitude of the polarization maintaining fiber 43 and 44 is adjusted to be fixed so that the laser beam P1 irradiated from the polarization maintaining fiber 43 is incident on the polarization maintaining fiber 44 and the laser beam P2 irradiated from the polarization maintaining fiber 44 is incident on the polarization maintaining fiber 43. Accordingly, the respective laser beams P1 and P2 can be located substantially optically coaxial, thus coaxially positioning the optical measuring light path formed by the vacuum-side laser beam Pa and the optical measuring light path formed by the gas-side laser beam Pb with high accuracy.

After fixing the attitude of the polarization maintaining fiber 43 and 44, the attitude of the optical transparent body 12 is fixed. The attitude of the optical transparent body 12 is fixed so that, for instance, the optical coupling efficiency of the laser beam P1 (Pa) irradiated from the polarization maintaining fiber 43 and the laser beam Pa reflected by the vacuum-side reflector 13A is more than or the same as a predetermined value. Specifically, the attitude of the optical transparent body 12 is adjusted to be fixed so that the laser beam Pa reflected by the vacuum-side reflector 13A returns to the polarization maintaining fiber 43. Accordingly, the reflectors 13A and 13B can be securely positioned substantially orthogonal with the respective laser beams Pa and Pb.

After fixing the attitude of the polarization preserving fibers 43 and 44 and the optical transparent body 12 (respective reflectors 13A and 13B), the reflective index of the test gas is measured.

According to the above-described embodiment, following effects can be obtained.

In the present embodiment in the two laser beams Pa and Pb split from the single laser beam P, the vacuum-side laser beam Pa is introduced to the vacuum-side laser interferometer 20 through the polarization maintaining fiber 43 to advance in the inside of the vacuum container 11, which is reflected by the vacuum-side reflector 13A to be incident on the vacuum-side laser interferometer 20. On the other hand, the gas-side laser beam Pb is introduced to the gas-side laser interferometer 30 through the polarization maintaining fiber 44 to advance in the space of the test gas, which is reflected by the gas-side reflector 13B to be incident on the gas-side laser interferometer 30. The movement of the optical measuring light path caused by moving the movable end of the vacuum container 11 between the vacuum-side laser interferometer 20 and the vacuum-side reflector 13A is measured by the vacuum-side laser interferometer 20. The movement of the optical measuring light path between the gas-side laser interferometer 30 and the gas-side reflector 13B is measured by the gas-side laser interferometer 30, thus obtaining the refractive index of the test gas based on the measured values.

Here, since the optical measuring light path formed by the vacuum-side laser beam Pa as the reference standard and the optical measuring light path formed by the gas-side laser beam Pb as the dimension to be measured are coaxially positioned sandwiching the movable end of the vacuum container 11, the Abbe's principle requiring linear disposition of the reference standard and the workpiece can be satisfied. Accordingly, the measurement error in measuring the air refractive index can be reduced, thus improving measurement accuracy.

Since the reflective film 13 is formed on one side of the optical transparent body 12, the reflectors 13A and 13B can be easily formed on both sides of the movable end, i.e. the vacuum-side and the gas-side, of the vacuum container 11.

Since the attitude of the polarization maintaining fibers 43 and 44 is fixed so that the optical coupling efficiency of the vacuum-side laser beam Pa and the gas-side laser beam Pb respectively irradiated from the polarization maintaining fibers 43 and 44 is more than or the same as a predetermined value, the respective laser beams Pa and Pb can be optically located substantially coaxial. In other words, the optical measuring path formed by the vacuum-side laser beam Pa and the optical measuring path formed by the gas-side laser beam Pb can be accurately located on the same axis.

While the optical measuring light path formed by the vacuum-side laser beam Pa and the optical measuring light path formed by the gas-side laser beam Pb are located coaxially, the attitude of the reflectors 13A and 13B (the optical transparent body 12) is fixed so that the coupling efficiency between the laser beam P1 (vacuum-side laser beam Pa) irradiated from the polarization maintaining fiber 43 and the vacuum-side laser beam Pa reflected by the vacuum-side reflector 13A is more than or the same as a predetermined value. Accordingly, the reflectors 13A and 13B can be securely positioned substantially orthogonal with the respective laser beams Pa and Pb, thus further improving the measurement accuracy.

Since the refractive index of the test gas is measured not by the number of the interference fringes measured by the respective laser interferometers 20 and 30 but by the frequency of the interference fringes measured by the respective laser interferometers 20 and 30, the measurement can be conducted with high resolution.

Since the uniform movement of the reflectors 13A and 13B (movable end of the vacuum container 11) is controlled by comparing feedback information of the value measured by the vacuum-side laser interferometer 20 fed back to the drive controller 54 and the predetermined command value of the moving speed, the uniform movement of the reflectors 13A and 13B can be controlled with high accuracy.

Since the drive body 51 is maintained in a predetermined attitude by the guide mechanism 55 holding through a fluid, the drive body 51 can be held in the predetermined attitude without mechanical distortion. Further, since the drive body 51 is driven by rotating the single drive roller 52 while being in contact with the drive body 51, mechanical constraint of the drive body 51 can be limited to a single portion of the contact portion against the drive roller 52.

Since the test gas is used as the fluid of the guide mechanism 55, the measurement accuracy is not decreased even when the fluid of the guide mechanism 55 and the test gas inside the space for the gas-side laser beam Pb to advance are mixed.

Incidentally, the scope of the present invention is not limited to the above-described embodiment but includes modifications and improvements as long as an object of the present invention can be attained.

For instance, though the test gas is used as the fluid of the guide mechanism 55, the fluid of the guide mechanism in the present invention is not restricted to the test gas but may be air. When the air is used for the guide mechanism, the fluid of the guide mechanism and the test gas in the space for the gas-side laser beam to advance are not mixed by employing an exhaust-collecting air bearing for the guide mechanism, thus not deteriorating the measurement accuracy.

What is claimed is:

1. An air refractometer, comprising:

a vacuum container, the length of the vacuum container being variable in longitudinal direction by moving a movable end thereof, one side of the movable end being a vacuum space and other side of the movable end opposing the one side of the movable end being a space of a test gas;

a vacuum-side laser beam advancing inside the vacuum container in the longitudinal direction;

a vacuum-side laser interferometer using the vacuum-side laser beam;

a gas-side laser beam parallel to the vacuum-side laser beam and advancing inside the space of the test gas;

a gas-side laser interferometer using the gas-side laser beam;

a drive mechanism for driving the movable end of the vacuum container along the longitudinal direction;

a vacuum-side reflector provided to a vacuum-side of the movable end of the ) vacuum container for reflecting the vacuum-side laser beam; and a gas-side reflector provided on a test gas side of the movable end for reflecting the gas-side laser beam, a movement of the vacuum-side reflector being measured by the vacuum-side laser interferometer, a movement of the gas-side reflector being measured by the gas-side laser interferometer, the refractive index of the test gas being measured based on the measured values, wherein the vacuum-side laser beam and the gas-side laser beam are split from a single laser beam and are respectively introduced to the vacuum-side laser interferometer and the gas-side laser interferometer through a single-mode light-waveguides, the respective laser beams irradiated from the respective single-mode light-waveguides being optical measuring light paths between the respective laser interferometers and the respective reflectors, and wherein the optical measuring light path formed by the vacuum-side laser beam and the optical measuring light path formed by the gas-side laser beam are coaxially located sandwiching the movable end of the vacuum container.

2. The refractometer according to claim 1, wherein the vacuum-side reflector and the gas-side reflector are provided on either a vacuum side or a gas side of an optical transparent body provided on the movable end, the vacuum-side reflector and the gas-side reflector being formed by a reflective film having a reflective surface of high reflectivity on both sides thereof.

3. The refractometer according to claim 1, wherein an attitude of the single-mode light-waveguide is fixed so that an optical coupling efficiency of the vacuum-side laser beam and the gas-side laser beam respectively irradiated from the single-mode light-waveguides is more than or the same as a predetermined value.

4. The refractometer according to claim 3, wherein an attitude of the reflector is fixed so that an optical coupling efficiency of the laser beam irradiated from either one of the single-mode light-waveguides and the one of the laser beam reflected by the reflector is more than or the same as a predetermined value.

5. The refractometer according to claim 1, wherein the vacuum-side laser interferometer measures a frequency of interference fringes by the vacuum-side laser beam and the gas-side laser interferometer measures a frequency of the interference fringes by the gas-side laser beam, and wherein, while moving the respective reflectors disposed on the movable end at a substantially uniform speed, respective measured values measured by the respective laser interferometers are multiplied by a frequency multiplying means having the same predetermined multiplying ratio, one of the multiplied measured values being counted as a reference clock of a frequency counter, the other multiplied measured values being counted as a counter clock of the frequency counter, whereby a refractive index of a test gas is obtained from the measured values.

6. The refractometer according to claim 5, wherein the measured value measured by the vacuum-side laser interferometer is fed back to a drive controller for controlling the drive mechanism and the uniform movement of the reflector is controlled based on comparison between the feedback information and a predetermined command value of a movement speed, the drive mechanism comprising: a drive body for the movable end fixed thereon; a single drive roller to be rotated in a drive direction of the drive body to drive the drive body while being in contact with the drive body; and a guide mechanism for holding the drive body in a predetermined attitude through a fluid.

7. The refractometer according to claim 6, wherein the fluid of the guide mechanism is the test gas.

8. The refractometer according to claim 6, wherein the fluid of the guide mechanism is air and the guide mechanism includes an exhaust-collecting air bearing.

* * * * *